(12) United States Patent
Flint

(10) Patent No.: US 9,517,060 B2
(45) Date of Patent: Dec. 13, 2016

(54) METHOD AND DEVICE FOR APPROXIMATING TISSUE

(71) Applicant: ETHICON, INC., Somerville, NJ (US)

(72) Inventor: James A. Flint, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 206 days.

(21) Appl. No.: 13/629,112

(22) Filed: Sep. 27, 2012

(65) Prior Publication Data

US 2014/0088644 A1 Mar. 27, 2014

(51) Int. Cl.
*A61B 17/04* (2006.01)
(52) U.S. Cl.
CPC ....... *A61B 17/0401* (2013.01); *A61B 17/0466* (2013.01); *A61B 2017/0409* (2013.01); *A61B 2017/0414* (2013.01); *A61B 2017/0417* (2013.01); *A61B 2017/0419* (2013.01); *A61B 2017/0475* (2013.01)
(58) Field of Classification Search
CPC ............ A61B 17/0281; A61B 17/0487; A61B 17/0401; A61B 17/06166; A61B 2019/4842; A61B 2017/0417; A61B 2017/0448; A61B 2017/00407; A61B 2017/0414; A61B 2017/044; Y10S 977/847; A61L 131/08; A61L 131/16; A61L 2300/404; A61L 2300/414; A61L 2300/606
USPC ........ 606/224–232, 139, 148, 143, 151, 144
See application file for complete search history.

(56) References Cited

U.S. PATENT DOCUMENTS

| | | | |
|---|---|---|---|
| 3,664,345 A | 5/1972 | Dabbs et al. | |
| 3,910,281 A | 10/1975 | Kletschka et al. | |
| 5,269,809 A | 12/1993 | Hayhurst et al. | |
| 5,320,629 A | 6/1994 | Noda et al. | |
| 5,788,063 A | 8/1998 | Van Ness | |
| 6,635,073 B2 | 10/2003 | Bonutti | |
| 6,702,835 B2 | 3/2004 | Ginn | |
| 6,767,037 B2 * | 7/2004 | Wenstrom, Jr. | 289/1.2 |
| 7,153,312 B1 | 12/2006 | Torrie et al. | |

(Continued)

FOREIGN PATENT DOCUMENTS

| | | |
|---|---|---|
| SU | 1360705 A1 | 12/1987 |
| WO | WO 2009149455 A1 | 12/2009 |

(Continued)

OTHER PUBLICATIONS

Co-pending U.S. Appl. No. 13/163,798, filed Jun. 20, 2011.

(Continued)

*Primary Examiner* — Jocelin Tanner
(74) *Attorney, Agent, or Firm* — Melissa J. Szanto

(57) ABSTRACT

A wound closure device including a first tissue anchor with a first suture filament fixedly coupled thereto at a proximal end and extending along a length to a free distal end, and a second tissue anchor with a second suture filament fixedly coupled thereto at a proximal end and extending along a length to a free distal end. The first suture filament is configured to form a slip knot at its proximal end substantially adjacent the first tissue anchor, and the second suture is configured to form a slip knot at its proximal end substantially adjacent the second tissue anchor. The length of the first suture filament passes through the slip knot of the second suture and the length of the second suture filament passes through the slip knot of the first suture filament.

25 Claims, 3 Drawing Sheets

(56) References Cited

U.S. PATENT DOCUMENTS

| | | | |
|---|---|---|---|
| 7,651,509 | B2 | 1/2010 | Bojarski et al. |
| 7,713,285 | B1* | 5/2010 | Stone et al. .................. 606/232 |
| 7,883,518 | B1 | 2/2011 | Davies et al. |
| 7,942,884 | B2 | 5/2011 | Vahid et al. |
| 2002/0019649 | A1 | 2/2002 | Sikora et al. |
| 2002/0120292 | A1* | 8/2002 | Morgan ........................ 606/232 |
| 2003/0065402 | A1* | 4/2003 | Anderson et al. ......... 623/23.66 |
| 2003/0088250 | A1* | 5/2003 | Colleran et al. ................. 606/72 |
| 2004/0010287 | A1 | 1/2004 | Bonutti |
| 2004/0162579 | A1 | 8/2004 | Foerster |
| 2005/0187577 | A1* | 8/2005 | Selvitelli et al. ............. 606/232 |
| 2006/0030884 | A1 | 2/2006 | Yeung et al. |
| 2006/0190042 | A1 | 8/2006 | Stone et al. |
| 2007/0027475 | A1 | 2/2007 | Pagedas |
| 2008/0140093 | A1 | 6/2008 | Stone et al. |
| 2009/0024144 | A1 | 1/2009 | Zeiner et al. |
| 2009/0024163 | A1 | 1/2009 | Zeiner et al. |
| 2009/0082805 | A1 | 3/2009 | Kaiser et al. |
| 2009/0088797 | A1 | 4/2009 | Crombie et al. |
| 2009/0222025 | A1 | 9/2009 | Catanese, III et al. |
| 2009/0228042 | A1 | 9/2009 | Koogle, Jr. et al. |
| 2009/0306776 | A1* | 12/2009 | Murray ...................... 623/13.12 |
| 2010/0114162 | A1 | 5/2010 | Bojarski et al. |
| 2011/0022061 | A1 | 1/2011 | Orphanos et al. |
| 2012/0323275 | A1 | 12/2012 | Crombie et al. |

FOREIGN PATENT DOCUMENTS

| | | |
|---|---|---|
| WO | WO 2010/062743 A2 | 6/2010 |
| WO | WO 2012/151592 A2 | 11/2012 |

OTHER PUBLICATIONS

Commerically available product called "g-Cath" sold by USGI Medical, Inc.; website http://www.usqimedical.com/eos/components-gcath.htm. (see cited U.S. Pat. No. 7,942,884).

* cited by examiner

METHOD AND DEVICE FOR APPROXIMATING TISSUE

FIELD OF THE INVENTION

The present invention relates generally to the field of tissue approximation, and more particularly to a method and device having particular application for approximating tissue during laparoscopic surgery or other procedures where access to the surgical site is difficult, or for approximating tissue that is difficult to penetrate.

BACKGROUND

Tissue approximation is an important part of most surgical procedures. The traditional means by which to approximate tissue involves the use of a surgical suture attached to a curved needle. The use of curved needles and sutures can be time consuming and challenging in many surgical procedures, particularly in difficult to access spaces, for large wounds, and/or when target tissue is difficult to penetrate. Myomectomy procedures that require closure of the uterus and vaginal cuff is just one example of such procedures. The use of a tissue anchor attached to a suture can improve the efficiency of tissue approximation. Some devices have been known to incorporate slip knots. For example, U.S. patent application Ser. No. 13/163,798, filed Jun. 20, 2011, the contents of which are incorporated herein by reference in their entirety, describes a device including a single strand of suture that is coupled to a first anchor at one end, forms a slip knot and also passes through a channel in a second tissue anchor. To tighten this device to approximate tissue a user must overcome the additional frictional forces of the suture filament sliding through the small channel in the second anchor. Another known device described in U.S. Patent Publication No. 2009/0024144 also has a single suture filament coupled to a first anchor at one end, forms a slip knot and instead of passing through a channel in the second anchor, passes through a knot in a second suture filament used for the sole purpose of tying the second suture anchor to the first suture filament as shown in FIG. 11 of the publication. This device suffers from the same drawback in that to tighten the device to approximate tissue requires overcoming the additional frictional forces of the first suture filament passing through the knot that secures the second tissue anchor to the device. Thus, the frictional engagement of the suture when sliding through the anchor or knot as described above increases the force necessary to shorten the distance between the two anchor points, and therefore can make the device difficult to use in a confined space. Thus, it is desirable to provide a suture based, dual anchor tissue approximation device that consistently requires minimal force when pulling on the suture free ends to shorten the distance between the anchor points, regardless of the type of tissue to be approximated. It would be further desirable to provide such a device that can readily be used in laparoscopic procedures.

SUMMARY OF THE INVENTION

The present invention provides a wound closure device having a first tissue anchor, a first suture filament fixedly coupled to the first tissue anchor at a proximal end and extending along a length to a free distal end, a second tissue anchor, and a second suture filament fixedly coupled to the second tissue anchor at a proximal end and extending along a length to a free distal end. The first suture filament is configured to form a slip knot at its proximal end substantially adjacent the first tissue anchor and the second suture is configured to form a slip knot at its proximal end substantially adjacent the second tissue anchor. The length of the first suture filament passes through the slip knot of the second suture and the length of the second suture filament passes through the slip knot of the first suture filament.

In one embodiment, the first and second tissue anchors are substantially axial, and include a tissue penetrating distal end. The first and second suture filaments may be coupled to a mid-section of the first and second tissue anchors respectively, and may further be made of an absorbable material such as polydioxanone. The anchors may further have a length of approximately 7 mm.

In yet another embodiment, the proximal end of the first and second anchors has a recess therein, sized and shaped to removably receive therein a distal end of an insertion device.

In yet another embodiment, the first and second suture filaments are made of an absorbable material, which may be polydioxanone.

In another embodiment, the device further includes a third tissue anchor, a third suture filament fixedly coupled to the third tissue anchor at a proximal end and extending along a length to a free distal end, a fourth tissue anchor, and a fourth suture filament fixedly coupled to the fourth tissue anchor at a proximal end and extending along a length to a free distal end. The third suture filament is configured to form a slip knot at its proximal end substantially adjacent the third tissue anchor, and the fourth suture is configured to form a slip knot at its proximal end substantially adjacent the fourth tissue anchor. The length of the third suture filament passes through the slip knot of the fourth suture and the length of the fourth suture filament passes through the slip knot of the third suture filament. Further, the third suture is intertwined with the first suture at a location along the length of the third and first sutures that is between the respective pairs of slip knots.

The present invention also provides a kit for performing tissue approximation including a wound closure device including a substantially axial first tissue anchor having a tissue penetrating distal end and a recess in a proximal end, and a first suture filament fixedly coupled to the first tissue anchor at a proximal end and extending along a length to a free distal end, and a substantially axial second tissue anchor having a tissue penetrating distal end and a recess in a proximal end and a second suture filament fixedly coupled to the second tissue anchor at a proximal end and extending along a length to a free distal end. The first suture filament forms a slip knot at its proximal end substantially adjacent the first tissue anchor, and the second suture filament forms a slip knot at its proximal end substantially adjacent the second tissue anchor. The length of the first suture filament passes through the slip knot of the second suture filament and the length of the second suture filament passes through the slip knot of the first suture filament. The kit further includes substantially axial insertion device having a distal tip sized and shaped to be removably received within the recess in the first and second anchors.

According to one embodiment, the first and second suture filaments are coupled to a mid-section of the first and second tissue anchors respectfully. The anchors may be made of an absorbable material such as polydioxanone, and may further have a length of approximately 7 mm.

In yet another embodiment, the first and second suture filaments may be made of an absorbable material such as polydioxanone.

The present invention also provides a wound closure device including a predetermined number of wound closure devices N, where N>1, wherein each wound closure device includes a tissue anchor and a suture filament fixedly coupled thereto and forming a slip knot substantially adjacent said anchor before extending outwardly to a free distal end. For each wound closure device from x=1 to N, the suture filament of wound closure device x=1 to (N−1) passes through the slip knot of the wound closure device x+1, and the suture filament of the wound closure device x=N passes through the slip knot of the wound closure device x=1.

In one embodiment, the first and second tissue anchors are substantially axial, and include a tissue penetrating distal end, and further may be coupled to a mid-section of the first and second tissue anchors respectfully.

In yet another embodiment, the first and second tissue anchors may be made of an absorbable material such as polydioxanone. The anchors may further have a length of approximately 7 mm.

In yet another embodiment, the proximal end of the first and second anchors has a recess therein, sized and shaped to removably receive therein a distal end of an insertion device.

In yet another embodiment, the first and second suture filaments may be made of an absorbable material such as polydioxanone.

These and other objects, features and advantages of the present invention will be apparent from the following detailed description of illustrative embodiments thereof, which is to be read in connection with the accompanying drawings.

DETAILED DESCRIPTION

Figure 1:
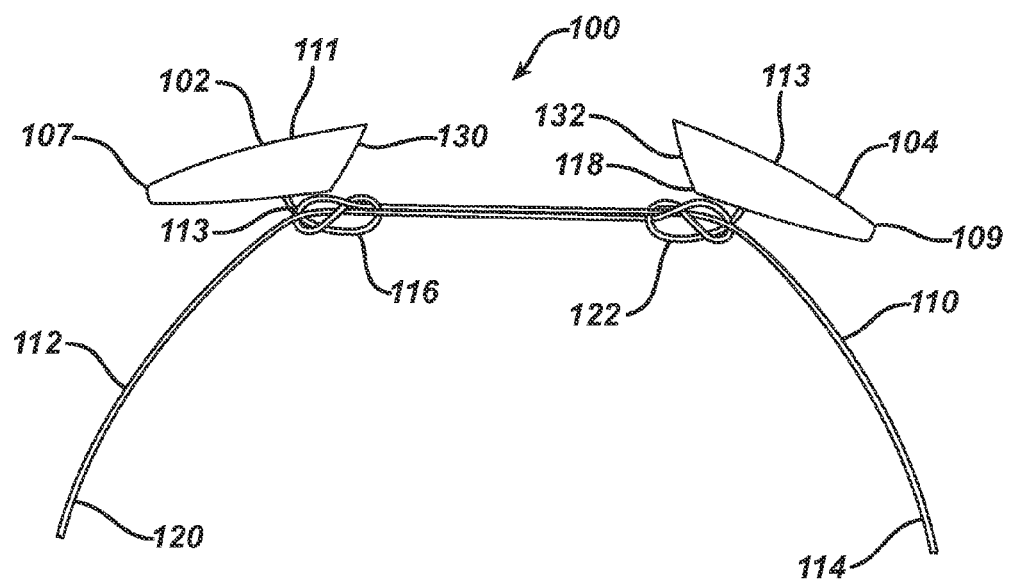
FIG. 1 illustrates a wound closure device according to the present invention.

FIG. 1 illustrates an exemplary embodiment of a tissue closure device 100 according to the present invention. The tissue closure device 100 includes a first anchor 102 and a second anchor 104, both of which preferably are self dissecting anchors having tapered leading ends 107, 109 respectively, capable of penetrating tissue to be approximated. Each anchor has a suture filament 110, 112 coupled thereto, preferably by a simple knot or the like at the mid-section 111, 113 of the anchors, and extending outwardly from the anchor. In one embodiment, the anchor has a through-hole for the suture that is slightly larger in diameter than the suture and smaller than the size of the formed knot. A countersink slightly larger than the knot allows the knot to lie below the surface of the anchor. The knot may be a simple overhand knot, a double-twist overhand knot, or a series of stacked or overlapping knots. The first suture filament 110 is coupled to the first anchor 102 at its proximal end 113 and extends outwardly to a free distal end 114. The first suture filament further forms a first slip knot 116 adjacent the first anchor before extending outwardly toward the free distal end 114. The second suture filament 112 is coupled to the second anchor 104 at its proximal end 118 and extends outwardly to a free distal end 120. The second suture filament also forms a second slip knot 122 adjacent the second anchor before extending outwardly toward the free distal end 120. Further, the second suture filament 112 passes through the first slip knot 116 and the first suture filament 110 passes through the second slip knot 122. In this manner, pulling on the distal end of either suture filament allows that suture filament to slide through the slip knot in the other suture filament with minimal friction until the slip knot of the other suture filament is tightened by tension placed on that suture anchor. Tension placed, for example on the second suture anchor that is attached to the second suture filament (in the direction of the arrow shown in FIG. 3 causes the slip knot of the second suture filament to change shape around the first suture filament 110, which ultimately engages the first suture filament to engage it sufficiently to hold in place relative to the first suture filament.

Figure 3:
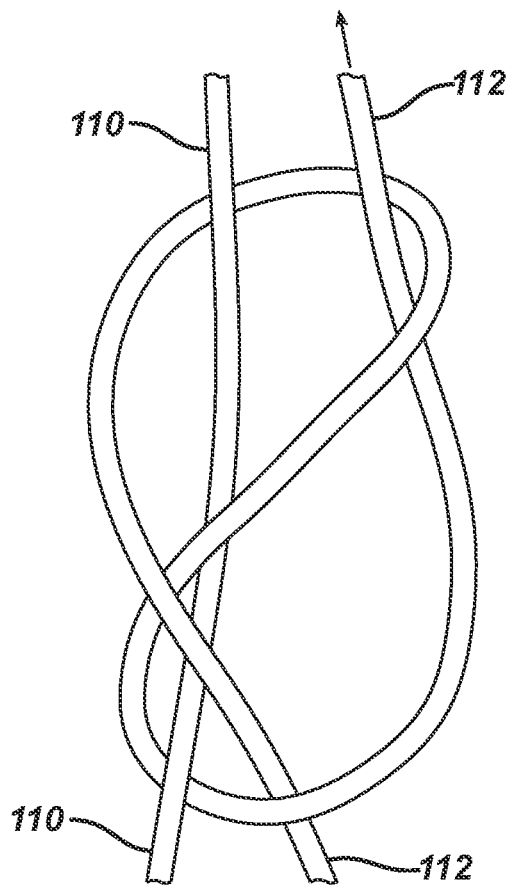
FIG. 3 is an enlarged view of the slip knot of the device of FIG. 1.

FIG. 3 is an enlarged version of an exemplary slip knot that can be used in the device of the present invention, where the first suture filament 110 passes through the second slip knot 122 formed in the second suture filament 112. Although one embodiment of a slip knot is shown in FIG. 3, the term "slip knot" as used herein is intended to mean any knot that can slip along the length of the filamentary element by pulling on one end of the filamentary element and lock to prevent continued slipping of the filament through the knot.

Figure 2:
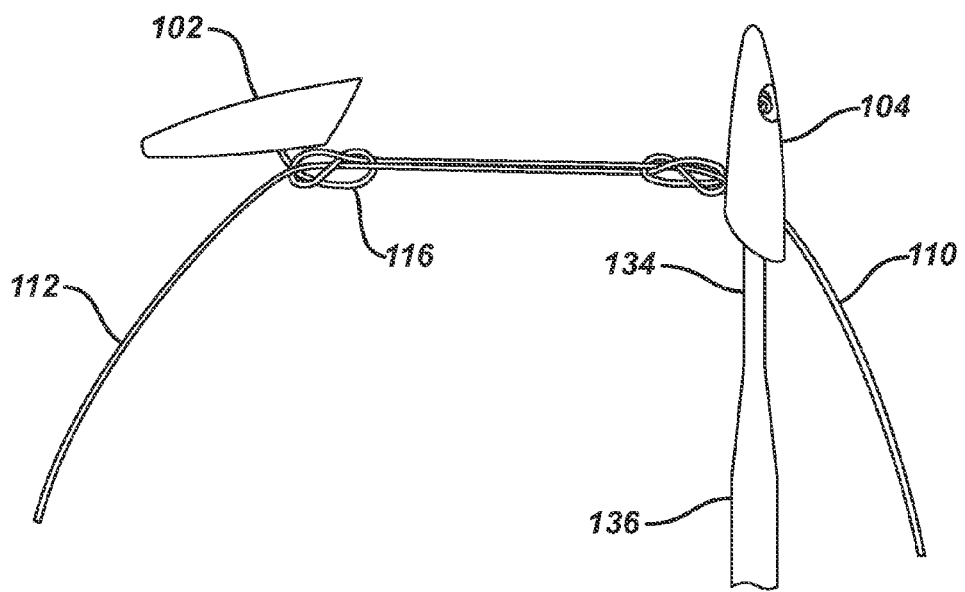
FIG. 2 illustrates the device of FIG. 1 with one anchor removably coupled to an insertion device.

The tissue closure device of the present invention has particular application laparoscopic closure of a wound in the uterine wall or for use in performing a vaginal vault suspension where the vaginal cuff is anchored to the sacrospinous ligament. In a preferred embodiment, the anchors are substantially axial or straight, approximately 7 mm in length and are molded of absorbable polydioxanone. Further, the suture filaments are preferably size 2-0 polydioxanone sutures (PDS). The anchors may also include a recess in the proximal end thereof 130, 132 sized and shaped to receive the distal end 134 of a linear inserter 136 (see FIG. 2) that, for laparoscopic procedures, is itself sized and shaped to readily fit within the laparoscopic port. Using a linear applicator eliminates any bending moment that would be introduced by attempting to implant the anchors along an axis that is perpendicular to or offset from the main axis of the applicator, and further eliminates the difficulty of using a curved needle for suturing through a laparoscopic port.

Each anchor is independently implanted and secured into the tissue on opposite sides of the area to be approximated using the linear applicator and self dissecting anchor mounted thereon. The distal ends of each filament are then used to draw the wound together, with each suture filament sliding through the slip knot of the other suture filament until the wound is approximated and sufficient tension is placed on the anchors to engage the corresponding filament via the slip knot to hold the wound closed. The above-described device further provides point-to-point fixation of tissue surfaces, eliminating the passage of a suture around tissue and thereby minimizing the potential for tissue strangulation and localized ischemia.

Figure 5:
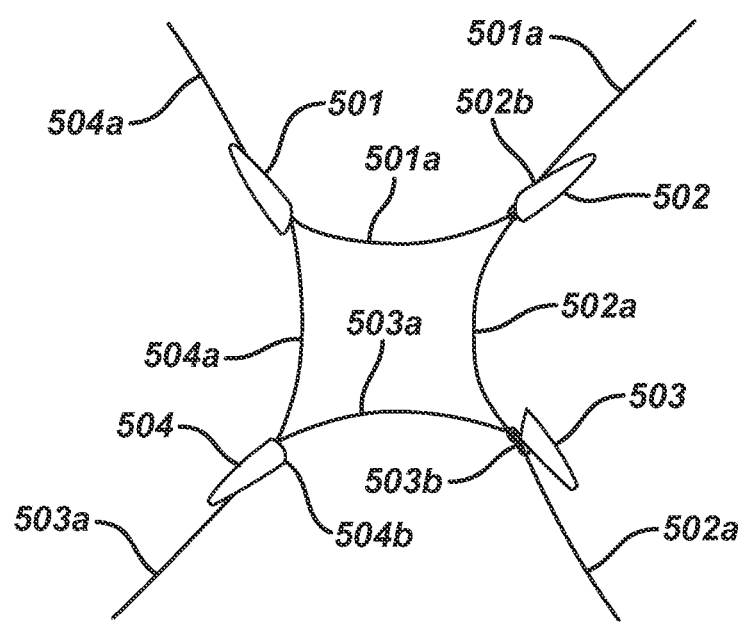
FIG. 5 is yet another alternate embodiment of the present invention having four suture anchors.

The assembly described above can further be coupled in series with additional tissue anchors and suture filaments. With reference now to FIG. 5, first 501, second 502, third 503 and fourth 504 anchors are shown each having a suture filament coupled thereto so as to form an adjustable slip knot and extend outwardly to a free distal end in the same manner as described in detail above with respect to FIG. 1. Each suture coupled to its respective tissue anchor will pass through the slip knot of the successive anchor/suture combination. For example, anchor 501 which is coupled with suture filament 501*a* passes through slip knot 502*b*, whereas suture filament 502*a* passes through slip knot 503*b* and so on. Although four anchor/suture combinations are illustrated in FIG. 5, the above-described assembly can apply to any number of such combinations from x=2 to N. In such an embodiment, for each anchor and associated suture filament x, the suture filament will pass through the slip-knot of the anchor/filament combination x+1, until x=N, at which point the suture filament from the anchor/filament combination N will pass through the slip knot of anchor/filament combination number 1.

Figure 4:
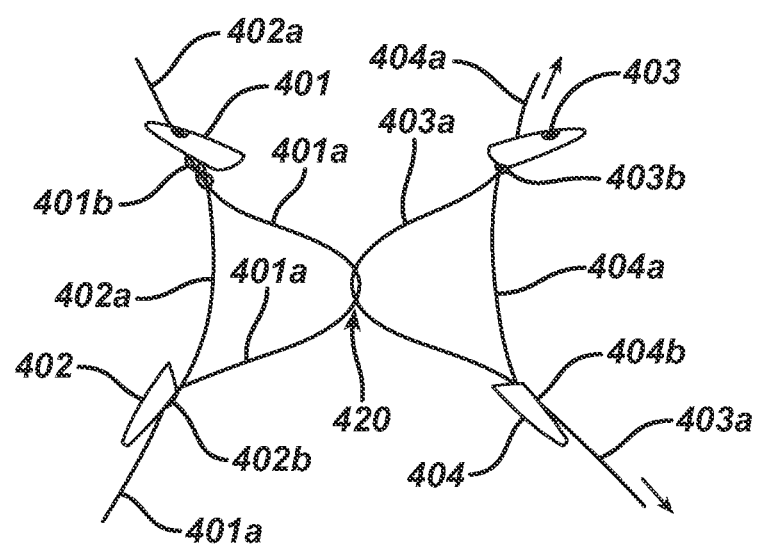
FIG. 4 illustrates an alternate embodiment of the present invention having four suture anchors.

In the embodiment illustrated in FIG. 5, pulling on the free ends of the suture filaments of adjoining combinations, i.e., filament 501*a* and 502*a*, will result in approximating the tissue between those two adjoining anchors (501, 502 and 502, 503 respectively). In another embodiment illustrated in FIG. 4, although there are four tissue anchors 401, 402, 403, 404, the anchors are configured in pairs, of which each pair is configured as described above with reference to FIG. 1. For each given pair (401, 402 and 403, 404), at least one suture filament extending between the pair of tissue anchors (i.e., filaments 401*a*, and 403*a*) are linked with one another as shown at junction 420 to thereby couple the assembly together. In this configuration, applying tension to the free ends of respective pairs of suture filaments such as 404*a* and 403*a*, will result in tissue approximation along orthogonal directions.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A wound closure device comprising:
   a first tissue anchor;
   a first suture filament fixedly coupled to the first tissue anchor at a proximal end and extending along a length to a free distal end;
   a second tissue anchor;
   a second suture filament fixedly coupled to the second tissue anchor at a proximal end and extending along a length to a free distal end;
   wherein the first suture filament forms a slip knot at its proximal end substantially adjacent the first tissue anchor;
   wherein the second suture filament forms a slip knot at its proximal end substantially adjacent the second tissue anchor;
   wherein the length of the first suture filament passes through the slip knot of the second suture filament and the length of the second suture filament passes through the slip knot of the first suture filament, and wherein the first and second tissue anchors can be drawn closer together in a direct path to enable point to point fixation of tissue pulling on either the free distal end of the first suture filament, the free distal end of the second suture filament, or both; and
   wherein the first and second tissue anchors are capable of being drawn together to a point substantially adjacent to one another.

2. The device according to claim 1, wherein the first and second tissue anchors are substantially axial, and include a tissue penetrating distal end.

3. The device according to claim 2, wherein the first and second suture filaments are coupled to a mid-section of the first and second tissue anchors respectively.

4. The device according to claim 3, wherein the first and second tissue anchors are comprised of an absorbable material.

5. The device according to claim 4, wherein the absorbable material is polydioxanone.

6. The device according to claim 5, wherein the first and second tissue anchors have a length of approximately 7 mm.

7. The device according to claim 2, wherein the proximal end of the first and second anchors has a recess therein, sized and shaped to removably receive therein a distal end of an insertion device.

8. The device according to claim 1, wherein the first and second suture filaments are comprised of an absorbable material.

9. The device according to claim 8, wherein the absorbable material is polydioxanone.

10. A kit for performing tissue approximation comprising:
    a wound closure device including a substantially axial first tissue anchor having a tissue penetrating distal end and a recess in a proximal end, and a first suture filament fixedly coupled to the first tissue anchor at a proximal end and extending along a length to a free distal end, and a substantially axial second tissue anchor having a tissue penetrating distal end and a recess in a proximal end and a second suture filament fixedly coupled to the second tissue anchor at a proximal end and extending along a length to a free distal end, wherein the first suture filament forms a slip knot at its proximal end substantially adjacent the first tissue anchor, wherein the second suture filament forms a slip knot at its proximal end substantially adjacent the second tissue anchor, and wherein the length of the first suture filament passes through the slip knot of the second suture filament and the length of the second suture filament passes through the slip knot of the first suture filament so that the first and second anchors can be drawn closer together in a direct path to enable point to point fixation of tissue by pulling on either the free distal end of the first suture filament, the free distal end of the second suture filament, or both and wherein the first and second tissue anchors are capable of being drawn together to a point substantially adjacent to one another, and
    a substantially axial insertion device having a distal tip sized and shaped to be removably received within the recess in the first and second anchors.

11. The kit according to claim 10, wherein the first and second suture filaments are coupled to a mid-section of the first and second tissue anchors respectfully.

12. The kit according to claim 11, wherein the first and second tissue anchors are comprised of an absorbable material.

13. The kit according to claim 12, wherein the absorbable material is polydioxanone.

14. The kit according to claim 13, wherein the first and second tissue anchors have a length of approximately 7 mm.

15. The kit according to claim 10, wherein the first and second suture filaments are comprised of an absorbable material.

16. The kit according to claim 15, wherein the absorbable material is polydioxanone.

17. A wound closure device comprising:
    a predetermined number of wound closure devices N, where N>2, wherein each wound closure device includes a tissue anchor and a suture filament fixedly coupled thereto and forming a slip knot substantially adjacent said anchor before extending outwardly to a free distal end;

wherein for each wound closure device from x=1 to N, the suture filament of wound closure device x=1 to (N−1) passes through the slip knot of the wound closure device x+1, and the suture filament of the wound closure device x=N passes through the slip knot of the wound closure device x=1.

18. The device according to claim 17, wherein each of said predetermined number of tissue anchors are substantially axial, and include a tissue penetrating distal end.

19. The device according to claim 18, wherein the first and second suture filaments are coupled to a mid-section of the first and second tissue anchors respectfully.

20. The device according to claim 19, wherein the first and second tissue anchors are comprised of an absorbable material.

21. The device according to claim 20, wherein the absorbable material is polydioxanone.

22. The device according to claim 21, wherein the first and second tissue anchors have a length of approximately 7 mm.

23. The device according to claim 18, wherein a proximal end of the predetermined number of tissue anchors has a recess therein, sized and shaped to removably receive therein a distal end of an insertion device.

24. The device according to claim 17, wherein each of said predetermined number of suture filaments are comprised of an absorbable material.

25. The device according to claim 24, wherein the absorbable material is polydioxanone.

* * * * *